(12) United States Patent
Lauciello et al.

(10) Patent No.: US 7,128,572 B2
(45) Date of Patent: Oct. 31, 2006

(54) METHOD AND APPARATUS FOR SELECTING DENTURE TEETH

(75) Inventors: Frank R. Lauciello, Elma, NY (US); Michael Thomas Kirkpatrick, Amherst, NY (US)

(73) Assignee: Ivoclar Vivadent AG, Schaan (LI)

( * ) Notice: Subject to any disclaimer, the term of this patent is extended or adjusted under 35 U.S.C. 154(b) by 458 days.

(21) Appl. No.: 10/779,297

(22) Filed: Feb. 12, 2004

(65) Prior Publication Data

US 2005/0181323 A1 Aug. 18, 2005

(51) Int. Cl.
*A61C 19/10* (2006.01)
*A61C 19/04* (2006.01)

(52) U.S. Cl. ............................................ 433/26; 433/73

(58) Field of Classification Search .................. 433/26, 433/72; 600/590; 33/513, 514
See application file for complete search history.

(56) References Cited

U.S. PATENT DOCUMENTS

| | | | | |
|---|---|---|---|---|
| 2,535,163 | A | * 12/1950 | Scott | 33/513 |
| 2,752,689 | A | * 7/1956 | Adams et al. | 33/513 |
| 4,133,110 | A | 1/1979 | Bernstein et al. | |
| 4,718,850 | A | * 1/1988 | Knebelman | 433/72 |
| 4,843,720 | A | * 7/1989 | Kim | 33/812 |
| 5,624,262 | A | 4/1997 | Yarovesky et al. | |
| 5,639,235 | A | * 6/1997 | Lapointe et al. | 433/26 |
| 5,800,164 | A | * 9/1998 | Pfau | 433/26 |
| 6,048,322 | A | * 4/2000 | Kushida | 600/587 |
| 6,447,296 | B1 | 9/2002 | Worthington | |

OTHER PUBLICATIONS

Wilson, G.H., A Manual of Dental Prosthetics, 1914, pp. 17-41, (Particularly p. 35), Lea & Febiger, Philadelphia.
Scott, J. E., The Scott System of Precision Articulation in Three-Dimensional Occlusion, J. Pros. Den., May 1952, pp. 362-380, vol. 2, No. 3.
Lee, J. H.; Dental Aesthetics; 1962; pp. 46-60, 63-65, 72-78; John Wright & Sons, Ltd.; Bristol.
Boucher, C.O., Selection of Teeth, Swenson's Complete Dentures, ed. 6, 1970, pp. 312-317, C. V. Mosby Company, St. Louis.
Applegate, S. G. and Cotman, L., Cuspid Tooth Placement in Edentulous Arches by Use of a Cuspid Locator, Journal of the Michigan State Dental Association, Jul.-Aug. 1967, pp. 233-235, vol. 49.
McCord, J. F. and Grant, A.A., Registration: Stage I—Creating and Outlining the Form of the Upper Denture, British Dental Journal, May 27, 2000, pp. 529-536, vol. 188, No. 10.

(Continued)

*Primary Examiner*—Cary E. O'Connor
(74) *Attorney, Agent, or Firm*—John C. Thompson; Alan S. Korman; Sandra J. Thompson

(57) ABSTRACT

A kit which may be used for anterior tooth selection, the kit including a facial meter for measuring the width of a nose and/or the distance between the eyes, and for correlating the measurement to a tooth size, and an anterior tooth selection guide consisting of a plurality of cards which have various sets of upper anterior teeth of differing sizes, soft and bold, depicted thereon so that a dentist or dental professional may place a card adjacent the face of the patient to make an initial evaluation of the teeth to be selected based upon the use of the anterior tooth selection guide. The kit may also includes a mold guide which includes various sets of anterior teeth and posterior teeth. This kit facilitates the tooth selection process by the dental professional.

8 Claims, 4 Drawing Sheets

OTHER PUBLICATIONS

Puri, M., Bhalla, L.R. and Khanna, V. K., Relationship of Intercanine Distance with the Distance between the Alae of Nose, Journal of the Indian Dental Association, Mar. 1972, pp. 46-50.

Wehner, P. J., Hickey, J. C. and Boucher, C. O., Selection of Artificial Teeth, J. Pros. Dent., Sep. 1967, pp. 222-232, vol. 18, No. 3.

Mavroskoufis, P. J., and Ritchie, G.M.; Nasal Width . . . as guides for the Sleeection and Arrangement of Maxillary Anterior Teeth; Journal of Prosthtic Desntistry,; Jun. 1981; vol. 18, No. 6.

Smith, B. J.; The Value of the Nose Width as an Esthetic Guide in Prosthodontics; J. Prosthet. Dent.; Nov. 1975; pp. 562-573; vol. 34, No. 5.

Leemark Dental Products;, internet catalog, p. 6, Jan. 4, 2004.

* cited by examiner

METHOD AND APPARATUS FOR SELECTING DENTURE TEETH

TECHNICAL FIELD

The present invention relates to an improved method and apparatus for selecting denture teeth, and more particularly to an improved system which is conveniently arranged to provide the dental professional with an easy to use system for the selection of the anterior and posterior teeth molds.

BACKGROUND OF THE INVENTION

For decades dental professionals have been taught a denture tooth selection procedure that is primarily based on the theory that the shape of a person's head or arch form corresponds to the shape of their teeth. Thus, shortly before World War I, J. Leon Williams presented a correlation between tooth form and the shape of a person's head. Thus the square, tapering, ovoid "William's Classification" was born. According to this theory, an inverted maxillary incisor tooth has roughly the same shape as the person's face, both in the profile and the frontal view. Although the validity of this theory has since been questioned by numerous authors, it remains today as the predominant feature of current mold guides due primarily to the stagnation of innovation in the field of removable prosthodotnics. Basic tooth forms have been established based on this concept, namely square, tapering, and ovoid.

It has proved to be an inexact, subjective analysis that is unpredictable and rarely repeatable. Unfortunately denture tooth mold guides have followed this same theory and continue to be organized according to square, tapering, and ovoid tooth forms. This classification has been handed down throughout the ages with minimal scientific merit or practical application and is not considered to be a significant tool for anterior tooth selection. The result of this ineffective denture tooth selection process is that dentists have withdrawn from the process of selecting denture teeth. This critical decision has been relegated to the technicians, who have grown comfortable with their favorite brands and molds of teeth and tend to select only from a limited number of molds. The technician unfortunately does not have the opportunity to view the patient and therefore make an informed decision based on the patient's many characteristics (sex, personality, age, neuromuscular status, denture history, etc).

Numerous investigators have suggested a correlation between the intercanine distance and the interalar width of the nose. The Swissedent investigators recorded the interalar width of the nose with an instrument, and then placed the pointers of the instrument against the natural maxillary canines. They found that, in 75% of their subjects, the pointers indicated approximately the center areas of the canines. This investigation resulted in the development of the Swissedent® Alameter. Boucher suggested projecting perpendicular lines downward from the alae of the nose to the buccal surface of a maxillary occlusion rim in the mouth. Marks are made on the occlusion rim which are used to position the tips or distal edges of the artificial canines. To select the correct size of an artificial tooth, the distance between the canine marks is measured around the curve of the occlusion rim with a flexible rule. Six maxillary anterior teeth are chosen with an over-all width equal to this measurement. Further investigation of this relationship was mathematically analyzed to more accurately determine maxillary anterior mold selection. Drs. Fisher and Frush introduced the concept of Dentogenics to the profession. Dentogenics is a concept that suggests various alterations of tooth morphology and position of teeth that follows individual patient characteristics (sex, personality, age). Tooth molds with feminine attributes were typified by gentle, rounded features, which suggest softness and smoothness. Conversely masculine tendencies were characterized in dentogenics by robust, cuboidal forms that expressed strength, vigor, and boldness. The organization of anterior mold morphology according to "softness" and "boldness" is a generally accepted classification of anterior tooth morphology and is commonly used in the tooth selection process.

OBJECTS AND SUMMARY OF THE INVENTION

It is an object of the present invention to provide an improved method and apparatus for selecting teeth for dentures.

More particularly, it is an object of the present invention to provide a kit which may be used for anterior tooth selection, the kit including a facial meter for measuring the width of a nose and/or the distance between the eyes, and for correlating the measurement to a tooth size, and an anterior tooth selection guide consisting of a plurality of cards which have various sets of upper anterior teeth depicted thereon, the cards illustrating differing sizes, such as small, medium, and large, there being two cards for each size, one soft and the other bold. In use, a dentist or dental professional may place a card adjacent the face of the patient to make an initial evaluation of the teeth to be selected based upon the use of the anterior tooth selection guide, and if desired, place other adjacent cards adjacent the face of the patient to confirm or change the initial selection.

It is a further object of the present invention to further provide in the kit a mold guide which may be used with the facial meter and the anterior tooth selection guide to facilitate the selection of posterior teeth compatible with the selected anterior teeth, the mold guide including various sets of anterior teeth and posterior teeth, the sets of anterior teeth being arranged in groups of small, medium, and large sizes, the groups of upper anterior teeth further being subdivided into columns of soft and bold forms, and the groups of lower anterior teeth being in columns, all columns of anterior teeth further being subdivided by length from short to long. The posterior teeth are subdivided into groups by occlusal surface from plane to anatomical, each group of posterior teeth being further subdivided into small, medium and large sizes. In use, a dentist or dental professional will select upper anterior teeth of the proper length from the group of teeth selected from the card, then select lower anterior teeth of essentially the same length, then select posterior teeth having the desired occlusal surface, and then select the size based on the size of the upper anterior teeth.

More particularly, the facial Meter is used to measure the width of the patient's nose (inter-alar distance) and to suggest an appropriately sized tooth for that patient. In addition, the facial meter may also be used to measure the distance between the inner canthi of the eyes to also suggest an appropriate sized tooth for the patient.

The anterior tooth selection guide preferably includes six cards that represent the following denture teeth:

Small, soft molds

Small, bold molds

Medium, soft molds

Medium, bold molds

Large, soft molds

Large, bold molds

Based on the use of the facial meter and the patient's appearance, one of the "cards" is selected and pulled forward and held adjacent to the patient's mouth for an initial evaluation and selection.

In a preferred embodiment, the facial meter and the anterior tooth selection guide of six cards are held together by a grommet at the base which allows the cards to spread similar to a fan. This allows the dental professional to hold the individual card to the patient's face as an aid to help determine what size and shape tooth is appropriate for that particular patient.

The above will be more fully understood after a consideration of the following detailed description taken in conjunction with the accompanying drawings in which preferred forms of this invention are illustrated.

DETAILED DESCRIPTION

Figure 5:
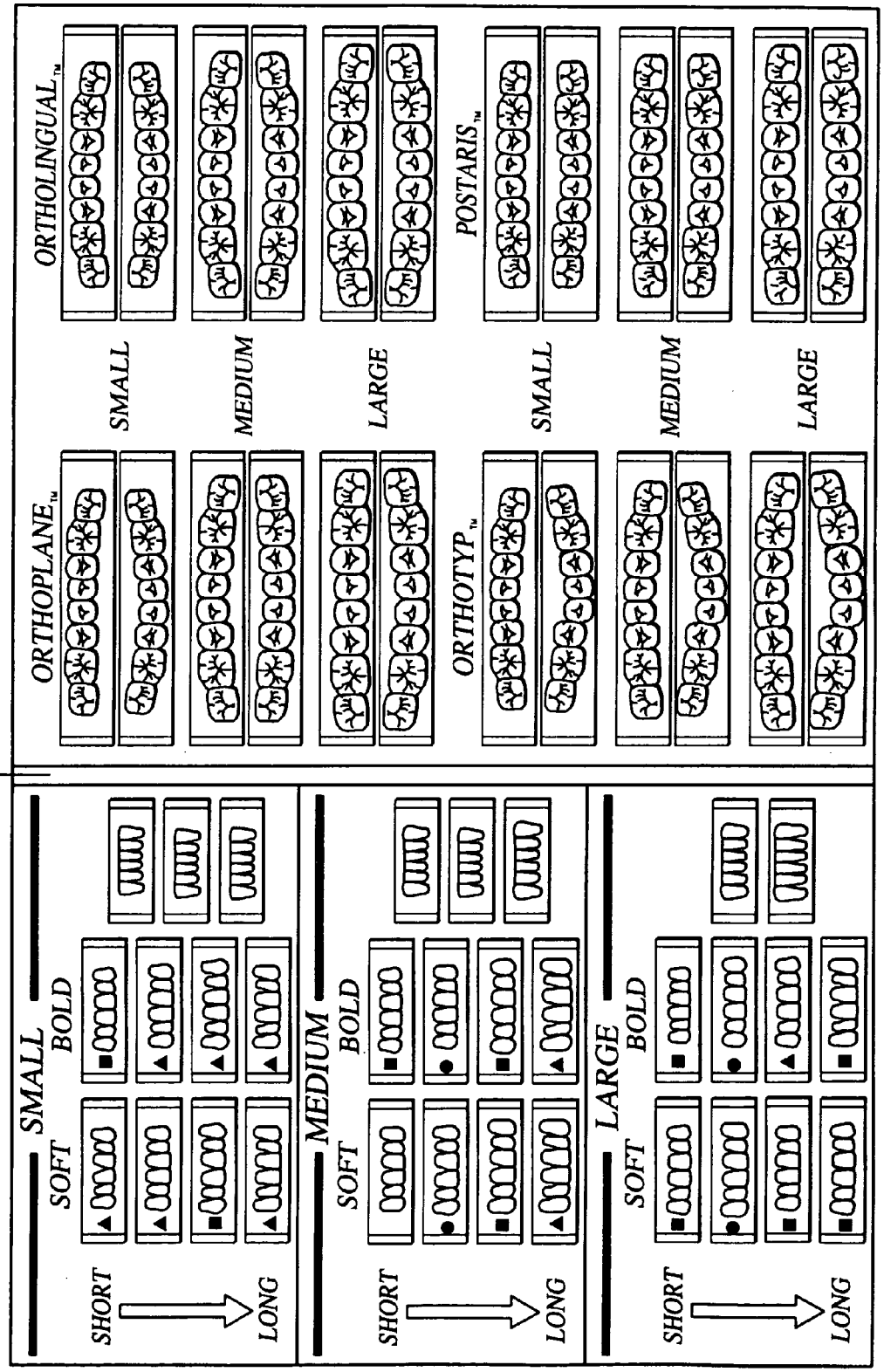
FIG. 5 shows a paper mold guide.
Figure 6:
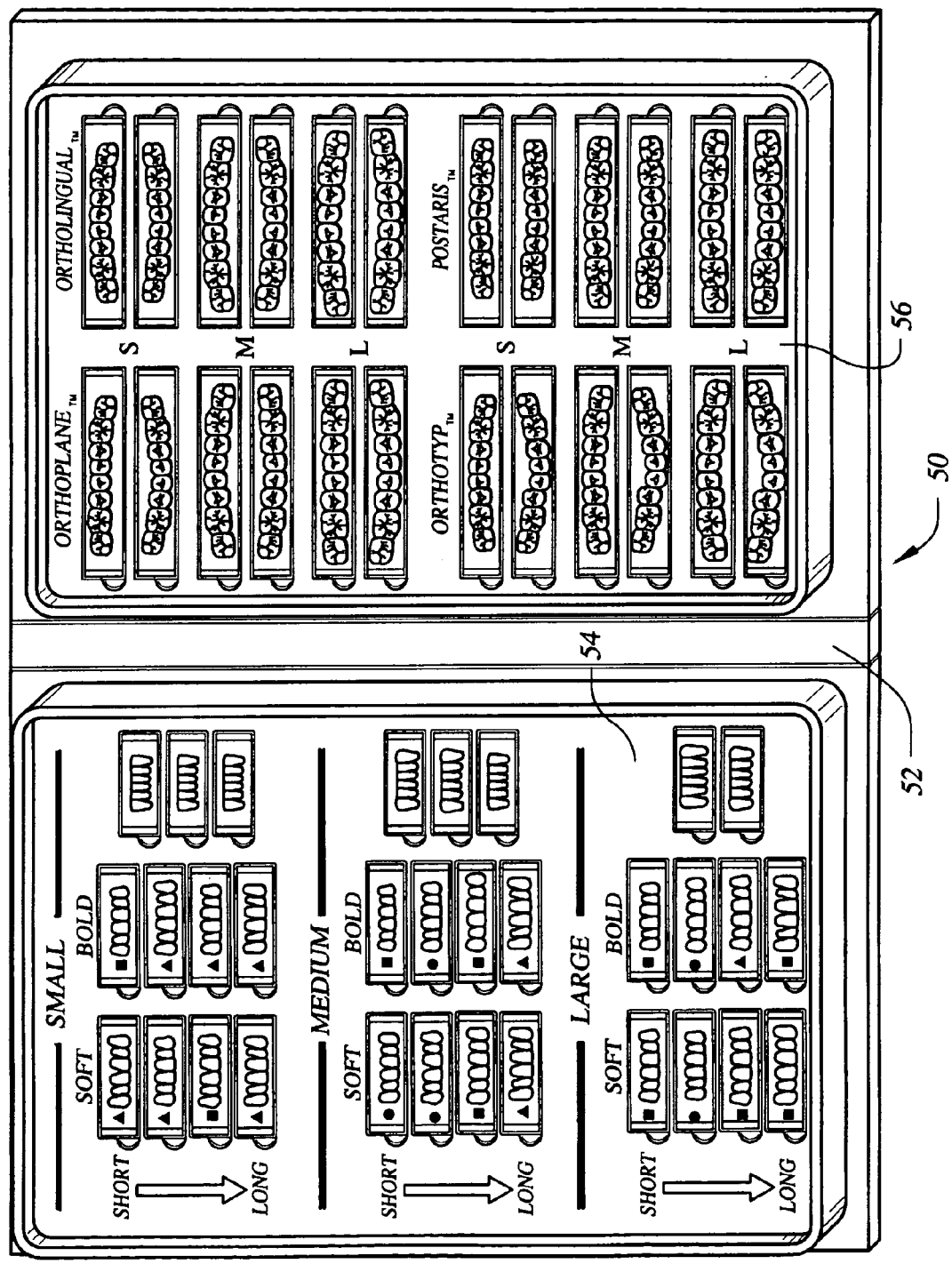
FIG. 6 shows a living mold guide.

The apparatus shown in the various figures comprises a kit which may be used by a dental professional, such as a dentist, in the selection of denture teeth. The kit has three principle components, a facial meter indicated generally at 10, an anterior tooth selection guide indicated generally at 26, and a mold guide 50, which may be a paper mold guide as shown in FIG. 5 or a living mold guide as shown in FIG. 6.

Figure 2:
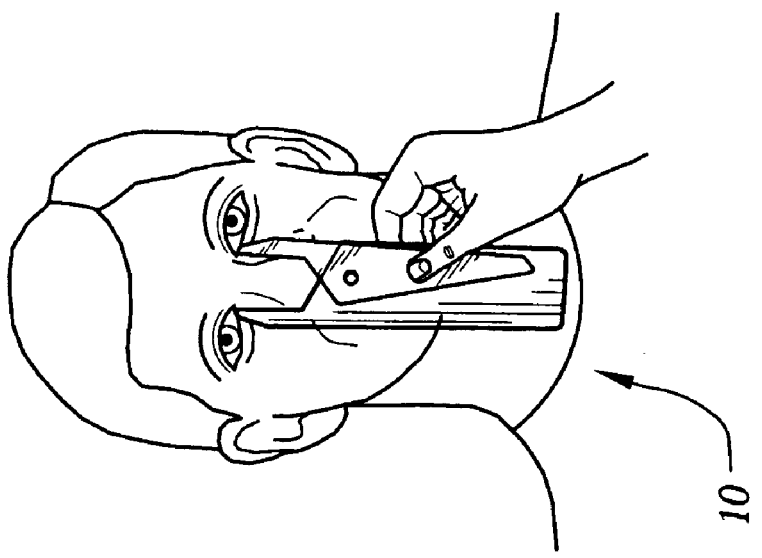
FIG. 2 is a view similar to FIG. 1, but showing the facial meter of this invention being used to measure the distance between the inner canthi of a patient's eyes.
Figure 1:
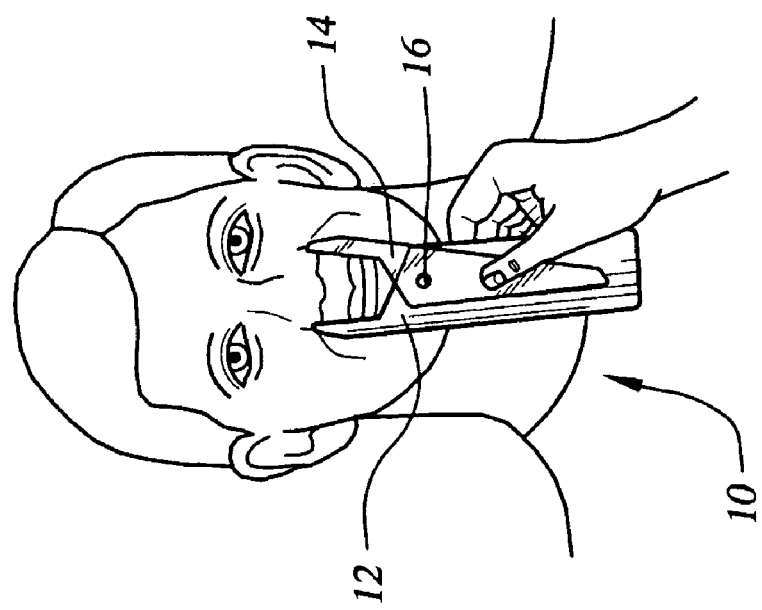
FIG. 1 illustrates the facial meter of this invention being used to measure the width of a patient's nose.
Figure 3:
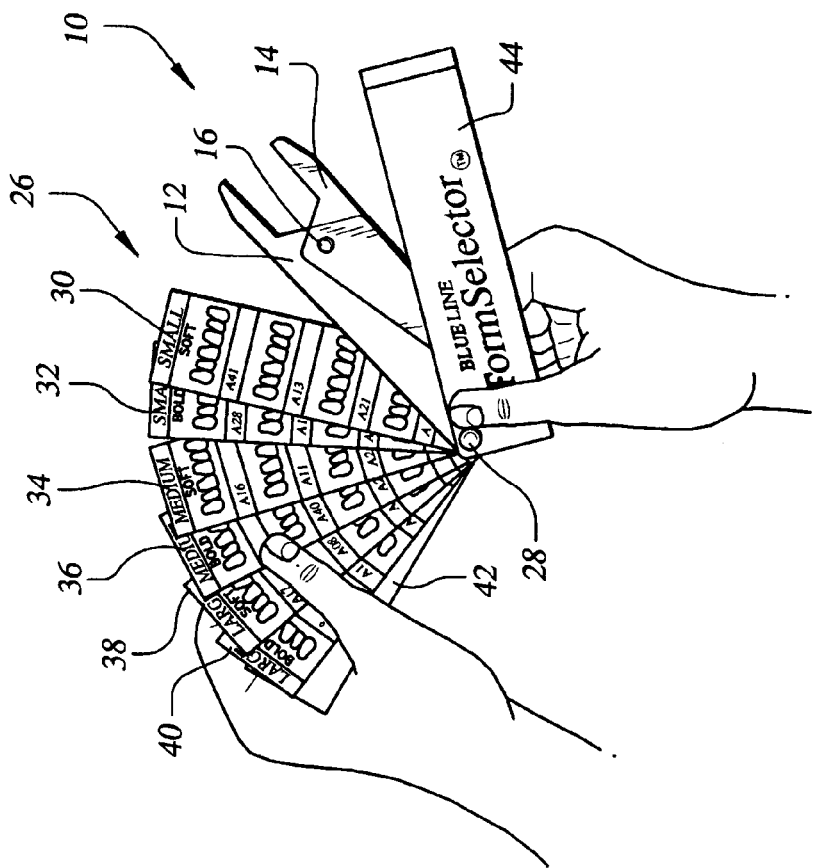
FIG. 3 shows the indicia on the facial meter.
Figure 4:
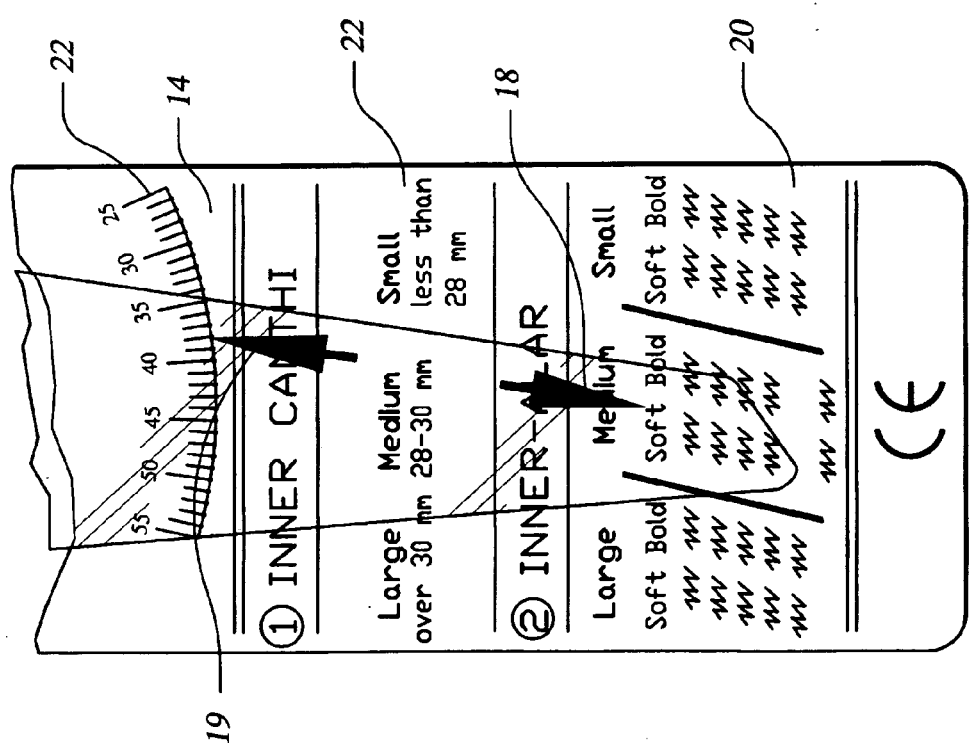
FIG. 4 shows the anterior tooth selection guide of this invention along with a facial meter, instructions, and a cover.

The facial meter includes first and second lower and upper members 12, 14, respectively, pivoted at an intermediate location by grommet 16, the upper member having pointers 18 and 19 thereon. The lower member has lower and upper sets of indicia 20, 22, respectively, thereon. The lower set of indicia 20 is used when the facial meter is used to measure the width of the nose, and represents large, medium, and small mold sets of anterior teeth, the indicia being further broken down into soft and bold molds. In use, the first arrow 18 will point to a group of indicia so that the dental professional will know the size of the teeth which should be used in the denture; and as the dental professional is viewing the patient, a selection may also be made as to whether soft or bold dentures should be employed. The second set of indicia 22 is used when the facial meter is used to measure the distance between the inner canthi of the eyes, the second set including a scale and a legend below, the second arrow pointing to the scale when the distance between the inner canthi is being measured. The dental professional can then read from the legend below the size of teeth which should be used. As a general rule, the preferred measurement is the width of the nose, but under certain circumstances the dental professional may use the distance between the inner canthi of the eyes. As shown in FIG. 3, the width of the nose is being measured in the manner indicated in FIG. 1.

The anterior tooth selection guide 26 contains a plurality of cards which have various sets of upper anterior teeth of differing sizes, soft and bold, depicted thereon so that a dental professional may place a card adjacent the face of the patient to make an initial evaluation of the teeth to be selected based upon the use of the facial meter, and, if desired, place other adjacent cards adjacent the face of the patient to confirm or change the initial selection. The plurality of cards are held together by a grommet 28. The guide 26 preferably includes six cards, the first card 30 illustrating in full size small soft upper anterior teeth, the second card 32 illustrating in full size small bold upper anterior teeth, the third card 34 illustrating in full size medium soft upper anterior teeth, the fourth card 36 illustrating in full size medium bold upper anterior teeth, the fifth card 38 illustrating in full size large soft upper anterior teeth, and the sixth card 40 illustrating in full size large bold upper anterior teeth. The anterior tooth selection guide 26 may also include a further card 42 of instructions. The facial meter 10 may be secured to the cards by the grommet 28. Finally, the facial meter and cards may be covered by a cover card 44.

As previously indicated, the kit includes a mold guide 50 which includes various sets of anterior teeth and posterior teeth, the sets of anterior teeth being arranged in groups of small, medium, and large sizes, the groups of upper anterior teeth being further subdivided into columns of soft and bold forms, and the groups of lower anterior teeth being in columns, all columns of anterior teeth being further subdivided by length from short to long; and the posterior teeth being subdivided into groups by occlusal surface from plane to anatomical, each group of posterior teeth being further subdivided into small, medium and large sizes. The mold guide may be a paper mold guide which has illustrations of the various sets of teeth printed on a surface. Such a mold guide is illustrated in FIG. 5. Alternatively, the mold guide may be a living mold guide which has sets of the various teeth mounted in a selection box. Such a mold guide is illustrated in FIG. 6, the mold guide being in the form of a book held together by a binding spine 52. The anterior teeth are carried by cards which are received in suitable recesses in a left elevated portion 54. Similarly, the posterior teeth are carried by cards received in suitable recesses in the right elevated portion 56. The living mold guide is so designed that it may be closed to resemble a book.

The kit is used in the following manner:

Step 1—select appropriate width of maxillary anterior mold. Using the Facial Meter measure the patient's interalar distance and refer to the suggested size category (small, medium, large).

Step 2—select desired tooth form (soft or bold). Each size category is subdivided into "soft" and "bold" molds. Teeth in the soft column are characterized by delicate line angles and rounded incisal edges that instills a more gentle form. Teeth in the bold column have more pronounced line angles and tend to have straighter incisal edges that present a more direct appearance. Choose from among the two columns for the form that best compliments the patient's appearance.

Step 3—select the length of the teeth. Tooth length can be modified and compensated for in the laboratory making it less critical than width and shape. Inter-ridge distance, lip length, amount of tooth exposed when smiling, and age, should be considered when choosing length. Each column of Soft and Bold categories is arranged from the short to long lengths.

Once the anterior teeth have been selected, it is now necessary to select the posterior teeth.

Step 1—select the appropriate occlusal scheme for the patient. The condition of a patient's residual ridge anatomy is a major factor in the selection of a posterior occlusal scheme. Severely resorbed ridges are less able to sustain horizontal forces of steeper cusp angles.

Step 2—select the posterior mold that corresponds to the anterior mold selected. All four occlusal options are provided in the three sizes. The four occlusal options are identified by Ivoclar Vivadent terms. Thus, SR Ortholingual® DCL teeth were designed specifically for lingual contact occlusion. SR Ortholingual® DCL feature progressively decreasing maxillary lingual cusps, shallow mandibular cusp angles, and an uncomplicated central fossa. They can accommodate balanced and non-balanced occlusal schemes and feature the fast setup ridge lap design. SR Ortholingual® DCL and SR Orthoplane® DCL lines were designed to work in combination (lingual upper with a monoplane lower). The SR Orthoplane® DCL lower features a central groove to accommodate the upper lingual cusp of the SR Ortholingual® DCL. Both feature the fast set-up ridge lap design. SR Orthotyp® DCL posteriors feature a gentler cusp angle of 22°. They occlude similar to anatomic teeth; however, this occlusion has a more forgiving intercuspation than a full anatomical occlusion posterior. SR Postaris® DCL denture teeth are a fully anatomical mold designed for partial dentures. The occlusal surface is wider than complete denture teeth to blend in with adjacent natural teeth. The lingual surface is also a full length so that acrylic gingiva does not extend above the natural gingiva.

While preferred forms of this invention have been described above and shown in the accompanying drawings, it should be understood that applicant does not intend to be limited to the particular details described above and illustrated in the accompanying drawings, but intends to be limited only to the scope of the invention as defined by the following claims. In this regard, the term "means for" as used in the claims is intended to include not only the designs illustrated in the drawings of this application and the equivalent designs discussed in the text, but it is also intended to cover other equivalents now known to those skilled in the art, or those equivalents which may become known to those skilled in the art in the future.

What is claimed is:

1. A kit for selecting denture teeth, the kit including
a facial meter for measuring the width of a nose and/or the distance between the eyes, and for correlating the measurement to a tooth size; and
an anterior tooth selection guide containing a plurality of cards which have various sets of upper anterior teeth of differing sizes, soft and bold, depicted thereon so that a dental professional may place a card adjacent the face of the patient to make an initial evaluation of the teeth to be selected based upon the use of the facial meter, and, if desired, place other adjacent cards adjacent the face of the patient to confirm or change the initial selection.

2. The kit for selecting denture teeth as set forth in claim 1 being further characterized by the provision of a mold guide which includes various sets of anterior teeth and posterior teeth, the sets of anterior teeth being arranged in groups of small, medium, and large sizes, the groups of upper anterior teeth being further subdivided into columns of soft and bold forms, and the groups of lower anterior teeth being in columns, all columns of anterior teeth being further subdivided by length from short to long, and the posterior teeth being subdivided into groups by occlusal surface from plane to anatomical, each group of posterior teeth being further subdivided into small, medium and large sizes.

3. The kit for selecting denture teeth as set forth in claim 1 wherein the facial meter includes first and second lower and upper members pivoted at an intermediate location, the upper member having a pointer thereon, and the lower member having indicia representing large, medium, and small mold sets of anterior teeth, the indicia being further broken down into soft and bold molds.

4. The kit for selecting denture teeth as set forth in claim 1 wherein the plurality of cards include six cards, the first card illustrating in full size small soft upper anterior teeth, the second card illustrating in full size small bold upper anterior teeth, the third card illustrating in full size medium soft upper anterior teeth, the fourth card illustrating in full size medium bold upper anterior teeth, the fifth card illustrating in full size large soft upper anterior teeth, and the sixth card illustrating in full size large bold upper anterior teeth.

5. The kit for selecting denture teeth as set forth in claim 2 wherein the mold guide is a paper mold guide which has illustrations of the various sets of teeth printed on a surface.

6. The kit for selecting denture teeth as set forth in claim 2 wherein the mold guide is a living mold guide which has sets of the various teeth mounted in a selection box.

7. A method for selecting denture teeth, the method including the following steps:
providing a facial meter for measuring the width of a nose and/or the distance between the eyes, and for correlating the measurement to a tooth size;
measuring the width of the patients nose and/or the distance between the eyes and determining the size tooth to be used based upon the measurement and whether a soft or bold tooth form should be used based upon the patient's appearance such as rugged masculine or soft feminine;
providing an anterior tooth selection guide containing a plurality of cards which have various sets of upper anterior teeth of differing sizes, soft and bold, depicted thereon; and
placing a card selected from the use of the facial meter adjacent the face of the patient to make an initial evaluation of the teeth to be selected, and if desired, placing other adjacent cards adjacent the face of the patient to confirm or change the initial selection.

8. The method for selecting denture teeth as set forth in claim 7 being further characterized by the following additional steps:
providing a mold guide which includes various sets of anterior teeth and posterior teeth, the sets of anterior teeth being arranged in groups of small, medium, and large sizes, the groups of upper anterior teeth being further subdivided into columns of soft and bold forms, and the groups of lower anterior teeth being in columns, all columns of anterior teeth being further subdivided by length from short to long, and the posterior teeth being subdivided into groups by occlusal surface from plane to anatomical, each group of posterior teeth being further subdivided into small, medium and large sizes; and
selecting upper anterior teeth of the proper length from the group of teeth selected from the card, selecting lower anterior teeth of essentially the same length, and selecting posterior teeth having the desired occlusal surface, and then selecting the size based on the size of the upper anterior teeth.

* * * * *